(12) United States Patent
Li et al.

(10) Patent No.: US 8,401,628 B2
(45) Date of Patent: Mar. 19, 2013

(54) SENSING VECTOR CONFIGURATION IN ICD TO ASSIST ARRHYTHMIA DETECTION AND ANNOTATION

(75) Inventors: Dan Li, Shoreview, MN (US); Allan C. Shuros, St. Paul, MN (US); Quan Ni, Shoreview, MN (US); Aaron R. McCabe, Minneapolis, MN (US); Yunlong Zhang, Mounds View, MN (US); Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 848 days.

(21) Appl. No.: 12/478,476

(22) Filed: Jun. 4, 2009

(65) Prior Publication Data

US 2009/0306486 A1 Dec. 10, 2009

Related U.S. Application Data

(60) Provisional application No. 61/058,835, filed on Jun. 4, 2008.

(51) Int. Cl.
*A61B 5/024* (2006.01)
(52) U.S. Cl. .......................... 600/515; 607/14
(58) Field of Classification Search ............. 607/14; 600/515
See application file for complete search history.

(56) References Cited

U.S. PATENT DOCUMENTS

| | | | |
|---|---|---|---|
| 5,193,550 A * | 3/1993 | Duffin ........................... | 600/510 |
| 5,730,142 A | 3/1998 | Sun et al. | |
| 5,755,739 A | 5/1998 | Sun et al. | |
| 5,782,888 A | 7/1998 | Sun et al. | |
| 6,246,907 B1 * | 6/2001 | Lin et al. ........................ | 607/5 |
| 6,308,095 B1 * | 10/2001 | Hsu et al. ....................... | 600/518 |
| 6,477,416 B1 | 11/2002 | Florio et al. | |
| 6,493,579 B1 | 12/2002 | Gilkerson et al. | |
| 6,505,082 B1 | 1/2003 | Scheiner et al. | |
| 6,516,225 B1 | 2/2003 | Florio | |
| 6,522,925 B1 | 2/2003 | Gilkerson et al. | |
| 6,912,418 B1 * | 6/2005 | Florio ............................. | 607/9 |
| 6,925,330 B2 | 8/2005 | Kleine | |
| 6,980,861 B1 | 12/2005 | Kleine | |
| 7,146,213 B1 | 12/2006 | Levine | |
| 7,158,829 B1 | 1/2007 | Levine | |
| 7,174,210 B1 | 2/2007 | Levine | |
| 7,184,834 B1 | 2/2007 | Levine | |
| 7,383,080 B1 | 6/2008 | Kil et al. | |
| 2006/0281999 A1 | 12/2006 | Li | |
| 2007/0135848 A1 | 6/2007 | Kim et al. | |
| 2007/0156194 A1 | 7/2007 | Wang | |
| 2009/0264946 A1 * | 10/2009 | Doerr et al. .................... | 607/4 |

OTHER PUBLICATIONS

Greenberg, S. M., et al., "A Comparison of ICD Implantations in the United States versus Italy", *Pacing Clin. Electrophysiol.*, 30(Suppl. 1), (2007), S143-S146.

Gunderson, et al., "Clinical Misclassification of ICD Detected VT/VF Episodes", *Heart Rhythm*, 3(5)(Suppl.), (2006), p. S159.

(Continued)

*Primary Examiner* — Joseph Stoklosa
(74) *Attorney, Agent, or Firm* — Schwegman, Lundberg & Woessner, P.A.

(57) ABSTRACT

An apparatus comprises an implantable cardiac signal sensing circuit, configured to provide a sensed near-field depolarization signal from a ventricle and to provide a sensed a far-field intrinsic atrial signal using a far-field atrial sensing channel, and a controller circuit communicatively coupled to the cardiac signal sensing circuit. The controller circuit includes a P-wave detection module configured to detect an atrial depolarization in the sensed far-field intrinsic atrial signal and a tachyarrhythmia detection module configured to detect an episode of tachyarrhythmia using the sensed near-field depolarization signal and to determine whether the tachyarrhythmia episode is indicative of supraventricular tachycardia (SVT) using the detected atrial depolarization and the sensed near-field depolarization signal.

27 Claims, 4 Drawing Sheets

OTHER PUBLICATIONS

Schuchert, A., et al., "Feasibility of Atrial Sensing via a Free-Floating Single-Pass Defibrillation Lead for Dual-Chamber Defribrillators", *J. Interv. Card. Electrophysiol.*, 8(3), (2003), 209-214.

Theuns, D. A. M. J., et al., "Prevention of Inappropriate Therapy in Implantable Cardioverter-Defrillators", *Journal of American College of Cardiology*, 44(12), (2004), 2362-2367.

* cited by examiner

SENSING VECTOR CONFIGURATION IN ICD TO ASSIST ARRHYTHMIA DETECTION AND ANNOTATION

RELATED APPLICATIONS

This application claims the benefit under 35 U.S.C. 119(e) of U.S. Provisional Patent Application Ser. No. 61/058,835, filed on Jun. 4, 2008, which is incorporated herein by reference in it entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, ventricular tachyarrhythmia can be terminated with high-energy shock therapy using an ICD. Under-detection of ventricular tachyarrhythmia (i.e., the IMD does not recognize an episode of ventricular tachyarrhythmia) may leave ventricular tachyarrhythmia untreated. Additionally, over-detection of ventricular tachyarrhythmia by the IMD (i.e., the IMD categorizes too many false-positives as ventricular tachyarrhythmia) is undesirable for the patient and the device. Cardioversion/defibrillation therapy can cause patient discomfort and consumes a relatively large amount of battery power which may lead to a shortened useful device lifetime. Therefore, it is important to accurately detect tachyarrhythmia.

Overview

This document relates generally to systems, devices, and methods for monitoring cardiac electrophysiological parameters of a patient or subject. Episodes of ventricular tachyarrhythmia are also monitored. In example 1, an apparatus includes an implantable cardiac signal sensing circuit, configured to provide a sensed near-field depolarization signal from a ventricle and to provide a sensed far-field intrinsic atrial signal using a far-field atrial sensing channel, and a controller circuit communicatively coupled to the cardiac signal sensing circuit. The far-field atrial sensing channel is configured to sense an intrinsic atrial signal from an electrode that is located outside of the atria. The controller circuit includes a P-wave detection module configured to detect an atrial depolarization in the sensed far-field intrinsic atrial signal and a tachyarrhythmia detection module configured to detect an episode of tachyarrhythmia using the sensed near-field depolarization signal and to determine whether the tachyarrhythmia episode is indicative of supraventricular tachycardia (SVT) using the detected atrial depolarization and the sensed near-field depolarization signal.

In example 2, the controller circuit of example 1 is optionally communicatively coupled to a plurality of far-field atrial sensing channels, each configured to obtain a sensed far-field intrinsic atrial signal. The controller circuit is configured to switch from a first far-field atrial sensing channel to a second far-field atrial sensing channel to improve sensing of the far-field intrinsic atrial signal.

In example 3, the P-wave detection module of examples 1 and 2 is optionally configured to measure a feature of an atrial depolarization detected using the first far-field atrial sensing channel and to measure the feature of the atrial depolarization detected using the second far-field atrial sensing channel. The controller circuit is configured to switch from the first far-field atrial sensing channel to the second far-field atrial sensing channel according to the measurements of the feature of the detected atrial depolarization.

In example 4, the apparatus of examples 1-3 optionally includes a sampling circuit and a communication circuit communicatively coupled to the cardiac signal sensing circuit. The sampling circuit is configured to provide a sampled far-field atrial signal from a sensed far-field intrinsic atrial signal. The communication circuit is configured to communicate information with an external device. The controller circuit is configured to communicate, to the external device, a first sampled far-field atrial signal obtained using the first far-field atrial sensing channel and a second sampled far-field atrial signal obtained using the second far-field atrial sensing channel, and switch from the first far-field atrial sensing channel to the second far-field atrial sensing channel according to a signal communicated from the external device.

In example 5, the cardiac signal sensing circuit and the controller circuit of examples 1-4 are optionally included in an implantable CFM device. The far-field atrial sensing channel optionally includes at least one of, a unipolar sensing vector including a coil electrode configured to be placed in or near a superior vena cava (SVC) and an electrode incorporated into a housing of the CFM device, a unipolar sensing vector including a ring electrode configured to be placed in or near the SVC and the electrode incorporated into the housing of the CFM device, a unipolar sensing vector including a ring electrode configured to be placed at, or proximal, to an ostium near a coronary sinus (CS), and the electrode incorporated into the housing of the CFM device, a bipolar sensing vector including the SVC coil electrode and the SVC ring electrode, and a bipolar sensing vector including the SVC ring electrode and the CS proximal ring electrode.

In example 6, the controller circuit of examples 1-5 optionally includes a timer circuit, and the P-wave detection module is optionally configured to avoid over-sensing of the far-field intrinsic atrial signal by at least one of disallowing sensing of the far-field atrial signal during a time duration following a sensed near-field event, changing a sensing threshold during a time duration following the sensed near-field event, wherein the sensing threshold is used for sensing the far-field atrial signal, or allowing sensing of the far-field atrial signal, but ignoring events sensed in the far-field atrial sensing channel during a time duration following the sensed near-field event.

In example 7, the P-wave detection module of examples 1-6 is optionally configured to perform principle component analysis (PCA) to extract the atrial depolarization from the ventricular events.

In example 8, the controller circuit of examples 1-7 is optionally configured to initiate sensing of the far-field intrinsic atrial signal after the tachyarrhythmia detection module detects the episode of tachyarrhythmia.

In example 9, the controller circuit of examples 1-8 is optionally configured to initiate sensing of the far-field intrinsic atrial signal when the tachyarrhythmia detection module detects a rate of sensed ventricular depolarization that exceeds a lowest tachyarrhythmia rate threshold value.

In example 10, the controller circuit of examples 1-9 is optionally configured to initiate sensing of the far-field intrinsic atrial signal when the tachyarrhythmia detection module detects a sudden change in a rate of sensed ventricular depolarizations. The sudden change is detected when a change in rate of sensed ventricular depolarizations exceeds a threshold change in rate within a specified time duration.

In example 11, the tachyarrhythmia detection module of examples 1-10 is optionally configured to determine whether the tachyarrhythmia episode is indicative of SVT using, a measure of at least one of ventricular rate or ventricular morphology, and a measure of at least one of atrial rate, atrial interval stability, or P-wave morphology regularity.

In example 12, the tachyarrhythmia detection module of examples 1-11 is optionally configured to determine whether the tachyarrhythmia episode is indicative of SVT by at least one of comparing a ventricular depolarization rate determined from the depolarization signal to an atrial depolarization rate determined from the far-field intrinsic atrial signal, or measuring a timing interval from the detected atrial depolarization to a corresponding detected ventricular depolarization.

In example 13, the tachyarrhythmia detection module of examples 1-12 is optionally configured to determine whether the tachyarrhythmia episode is indicative of atrial fibrillation using the detected atrial depolarization and the sensed near-field depolarization signal.

In example 14, the apparatus of examples 1-13 optionally includes an implantable hemodynamic sensor circuit communicatively coupled to the controller circuit. The hemodynamic sensor circuit provides a hemodynamic signal other than an intrinsic electrical cardiac signal, and the hemodynamic signal is representative of mechanical function of a cardiovascular system of a subject. The tachyarrhythmia detection module is configured to determine whether the tachyarrhythmia episode is indicative of SVT using the hemodynamic signal.

In example 15, the apparatus of examples 1-14 optionally includes a therapy circuit communicatively coupled to the controller circuit and configured to provide anti-tachyarrhythmia therapy. The tachyarrhythmia detection module is configured to provide a determination whether the episode of tachyarrhythmia is indicative of VT or SVT, and the controller circuit is configured to initiate an anti-tachyarrhythmia therapy according to the determination.

In example 16, the apparatus of examples 1-14 optionally includes a therapy circuit, communicatively coupled to the controller circuit and configured to provide anti-tachyarrhythmia therapy. The tachyarrhythmia detection module is configured to provide a determination whether the episode of tachyarrhythmia is indicative of one of atrial fibrillation, atrial flutter, or atrial tachycardia, and is configured to initiate an anti-tachyarrhythmia therapy according to the determination.

In example 17, a method includes sensing a far-field intrinsic atrial signal with an implantable cardiac function management (CFM) device. The far-field intrinsic atrial signal is sensed using a first far-field atrial sensing channel. The far-field atrial sensing channel is configured to sense an intrinsic atrial signal from an electrode that is located outside of the atria. The example also includes detecting an atrial depolarization in the sensed far-field intrinsic atrial signal, detecting an episode of tachyarrhythmia using a near-field depolarization signal sensed from a ventricle, and determining whether the tachyarrhythmia episode is indicative of SVT using the detected atrial depolarization and the sensed near field signal.

In example 18, the method of example 17 optionally includes switching from the first far-field atrial sensing channel to a second far-field atrial sensing channel to improve sensing of the far-field intrinsic atrial signal.

In example 19, the switching from the first far-field atrial sensing channel to a second far-field atrial sensing channel of example 18 optionally includes switching from the first far-field atrial sensing channel to a second far-field atrial sensing channel according to a measurement of the detected atrial depolarization.

In example 20, the method of examples 18-19 optionally includes sampling the far-field intrinsic atrial signal sensed with the first far-field atrial sensing channel to obtain a first sampled far-field atrial signal, sampling a far-field intrinsic atrial signal sensed with the second far-field atrial sensing channel to obtain a second sampled far-field atrial signal, and communicating the first and second sampled far-field atrial signals to an external device. The switching from the first far-field atrial sensing channel to a second far-field atrial sensing channel optionally includes switching from the first far-field atrial sensing channel to a second far-field atrial sensing channel according to a signal communicated from the external device.

In example 21, the method of examples 18-20 optionally includes selecting the first far-field atrial sensing channel and the second far-field atrial sensing channel from the group consisting essentially of a unipolar sensing vector including a coil electrode configured to be placed in or near a superior vena cava (SVC) and an electrode incorporated into a housing of the ICD, a unipolar sensing vector including a ring electrode configured to be placed in or near the SVC and the electrode incorporated into a housing of the ICD, a unipolar sensing vector including a ring electrode configured to be placed at, or proximal, to an ostium near a coronary sinus (CS), and the electrode incorporated into a housing of the ICD, a bipolar sensing vector including the SVC coil electrode and the SVC ring electrode, and a bipolar sensing vector including the SVC ring electrode and the CS proximal ring electrode.

In example 22, the detecting an atrial depolarization of examples 17-21 optionally includes rejecting ventricular events sensed by the first far-field atrial sensing channel.

In example 23, the rejecting ventricular events of example 22 optionally includes at least one of disallowing sensing during a time duration following sensing of a near-field event in a ventricle, changing a sensing threshold during a time duration following sensing of a near-field event in a ventricle, allowing sensing but ignoring events sensed during a time duration following sensing of a near-field event in a ventricle, or performing principle component analysis (PCA) to extract the atrial depolarization from the ventricular events.

In example 24, the sensing a far-field intrinsic atrial signal of examples 17-23 optionally includes sensing the far-field intrinsic atrial signal when the episode of tachyarrhythmia is detected.

In example 25, the sensing a far-field intrinsic atrial signal of examples 17-24 optionally includes sensing the far-field intrinsic atrial signal when a rate of sensed ventricular depolarization exceeds a threshold rate.

In example 26, the sensing a far-field intrinsic atrial signal of examples 17-25 optionally includes sensing the far-field intrinsic atrial signal when detecting a sudden change in rate of sensed ventricular depolarizations. Detecting the sudden change includes detecting a change in rate of sensed ventricular depolarizations that exceeds a threshold change in rate within a specified time duration.

In example 27, the determining whether the tachyarrhythmia episode is indicative of SVT of examples 17-26 optionally includes using measure of at least one of ventricular rate or a measure of ventricular morphology, and using a measure of at least one of atrial rate, atrial interval stability, or P-wave morphology regularity.

In example 28, the determining whether the tachyarrhythmia episode is indicative of SVT of examples 17-26 optionally includes at least one of comparing a ventricular depolarization rate determined from the depolarization signal to an atrial depolarization rate determined from the far-field intrinsic atrial signal, or measuring a timing interval from the detected atrial depolarization to a corresponding ventricular depolarization.

In example 29, the method of examples 17-28 optionally includes determining whether the tachyarrhythmia episode is indicative of atrial fibrillation using the detected atrial depolarization and the sensed near-field depolarization signal.

In example 30, the determining whether the tachyarrhythmia episode is indicative of SVT of examples 17-29 optionally includes using the detected atrial depolarization, the sensed near-field depolarization signal from the ventricle, and a hemodynamic signal representative of mechanical function of a cardiovascular system of a subject.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
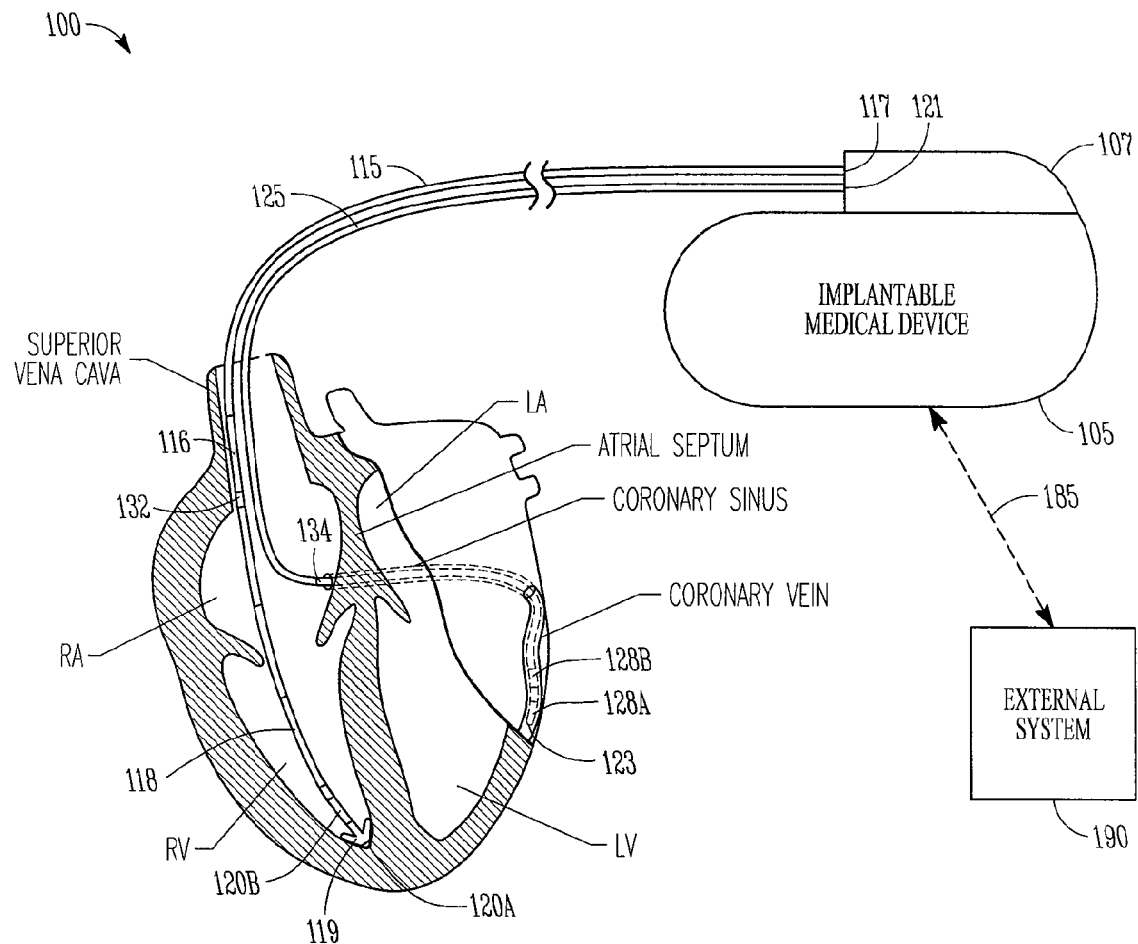
FIG. 1 is an illustration of an example of portions of a system that includes an IMD.

FIG. 1 is an illustration of an example of portions of a system 100 that includes an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115, 125, to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end 117 and a distal end 119. The proximal end 117 is coupled to a header connector 107. The distal end 119 is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the RA or the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end 119 such as for placement in the RV. The RV electrodes 120A and 120B can form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification or filtering of the sensed signal. Sensing and pacing allows the IMD 105 to adjust timing of the heart chamber contractions.

In some examples, an IMD 105 can include a left ventricular (LV) lead 125. The LV lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 can include an LV ring or tip electrode 128A and an LV ring electrode 128B. The distal portion of the LV lead 125 is configured for placement in the coronary sinus (CS) and coronary vein such that the LV electrodes 128A and 128B are placed in the coronary vein. The LV electrodes 128A and 128B can form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses. In some examples, the LV lead 121 includes a ring electrode 134 located at, or proximal to, the ostium (e.g., CS proximal ring).

The IMDs can be configured with a variety of electrode arrangements, including transvenous, epicardial electrodes (i.e., intrathoracic electrodes), or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

Some IMDs, such as shown in FIG. 1, may not include an electrode for sensing electrical activity in an atrium. For example, the IMD can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and shock or morphology analysis). The absence of sensing intrinsic atrial depolarizations (P-waves) may make the arrhythmia detection perform less well than a dual chamber ICD (e.g., an ICD including an electrode for placement in an atrium and an electrode for placement in a ventricle). Lack of atrial sensing can also make it difficult for a physician to retrospectively diagnose and annotate an episode of tachyarrhythmia as VT or SVT. It is desirable to have knowledge of P-waves even though the IMD can be a ventricular chamber device.

Figure 2:
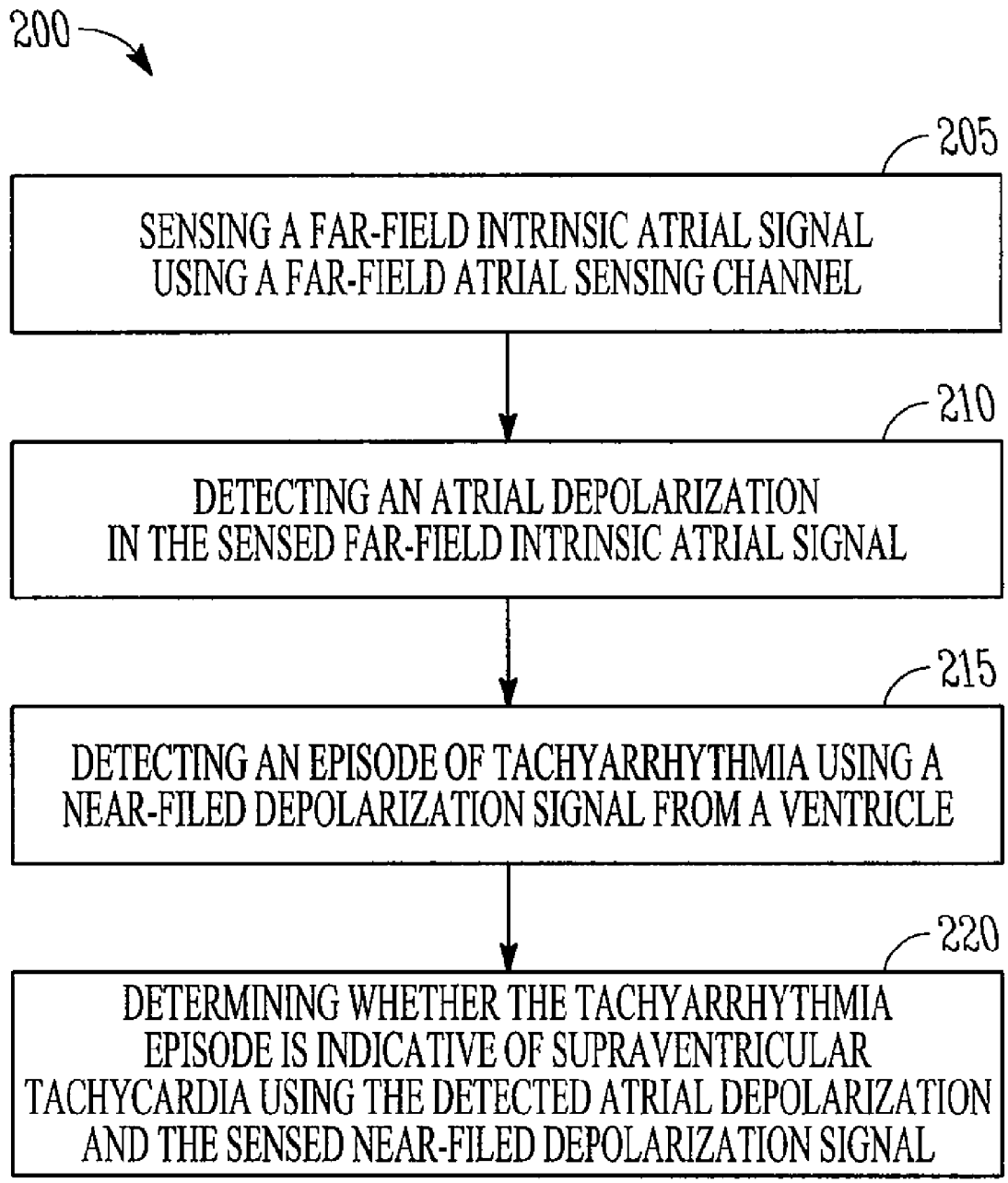
FIG. 2 shows a flow diagram of an example of a method for detecting a tachyarrhythmia.

FIG. 2 shows a flow diagram of an example of a method 200 for detecting a tachyarrhythmia. At block 205, a far-field intrinsic atrial signal is sensed with an implantable cardiac function management (CFM) device. The far-field intrinsic atrial signal is sensed using a far-field atrial sensing channel. At block 210, an atrial depolarization is detected in the sensed far-field intrinsic atrial signal.

Figure 3:
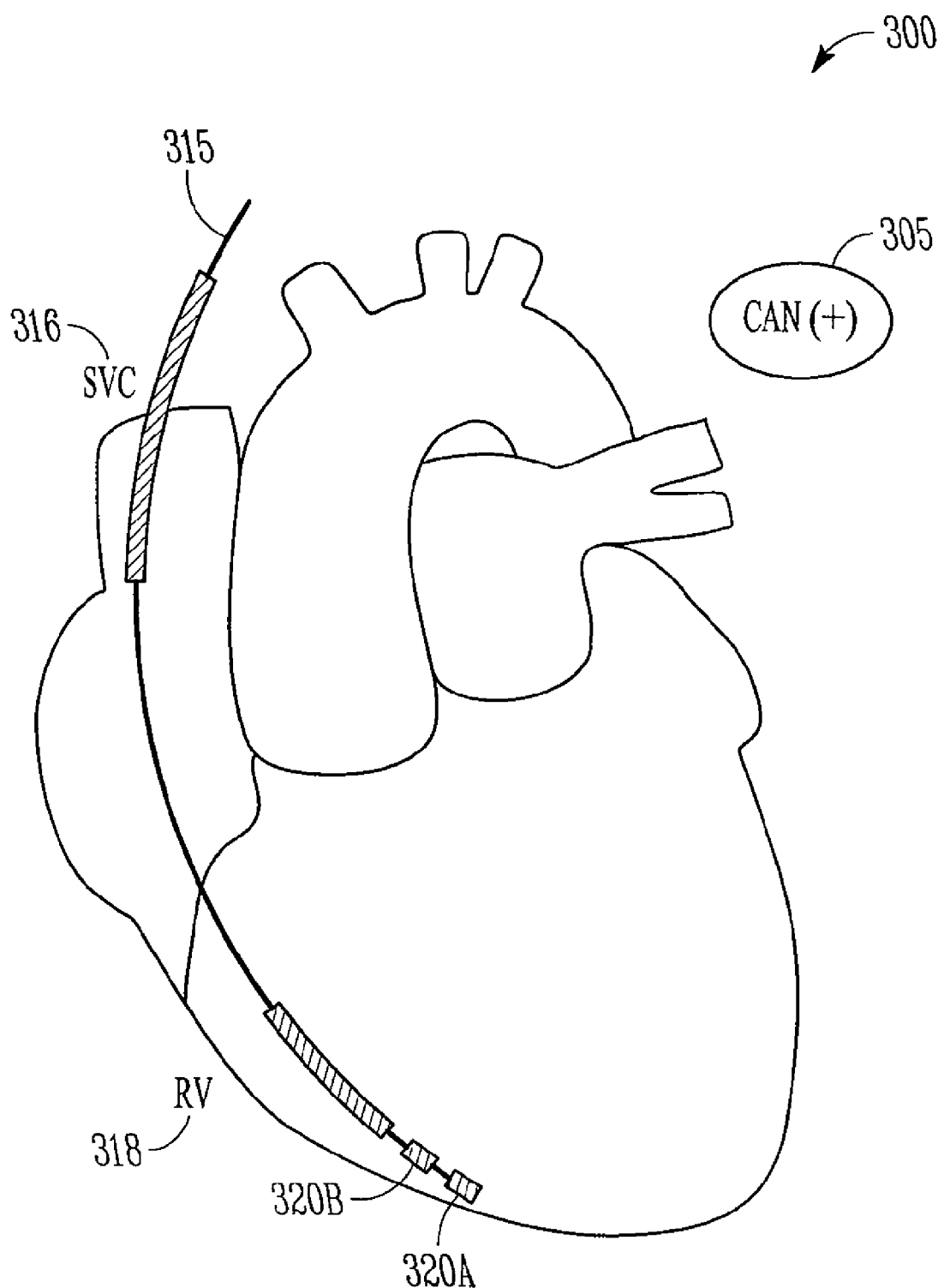
FIG. 3 shows an example of a system having a far-field atrial sensing channel that can sense a far-field intrinsic atrial signal.

FIG. 3 shows an example of a system 300 having a far-field atrial sensing channel that can sense a far-field intrinsic atrial signal. The system 300 includes an IMD 305 with an RV lead 315. The IMD 305 is an ICD and the connection to the RV lead 315 is not shown for simplicity. The RV lead 315 includes tip electrode 320A, optional ring electrode 320B, RV coil electrode 318, and SVC coil electrode 316. The far-field atrial sensing channel is between SVC coil electrode 316 and an electrode formed on the can of the IMD 305. The far-field atrial sensing channel senses a far-field atrial depolarization of the right atrium (RA) even though no electrode is placed within the RA.

Returning to FIG. 2, at block 215, an episode of tachyarrhythmia is detected using a near-field depolarization signal sensed from a ventricle. In FIG. 3, an example of a near-field sensing channel includes tip electrode 320A and ring electrode 320B. The near-field sensing channel senses a near-field depolarization signal in the RV. In some examples, the episode of tachyarrhythmia is detected when a ventricular depolarization rate exceeds a specified lowest tachyarrhythmia detection rate.

In FIG. 2, at block 220, it is determined whether the tachyarrhythmia episode is indicative of SVT or VT using the detected far-field atrial depolarization and the sensed near-field signal from the ventricle. In some examples, the tachyarrhythmia episode is deemed indicative of VT when the rate of sensed ventricular depolarizations exceeds the rate of detected atrial depolarizations by a specified a rate difference threshold value. In some examples, if the episode is determined to be SVT, tachyarrhythmia therapy is inhibited. If the episode is determined to be VT, tachyarrhythmia therapy is initiated. The tachyarrhythmia therapy can include anti-tachyarrhythmia pacing (ATP) or high energy shock defibrillation therapy. In certain examples, the detected episode is initially assumed to be VT and it is assumed that therapy will be applied. The discrimination of the tachyarrhythmia episode is to determine whether the episode is SVT in which case tachyarrhythmia therapy is not applied.

Figure 4:
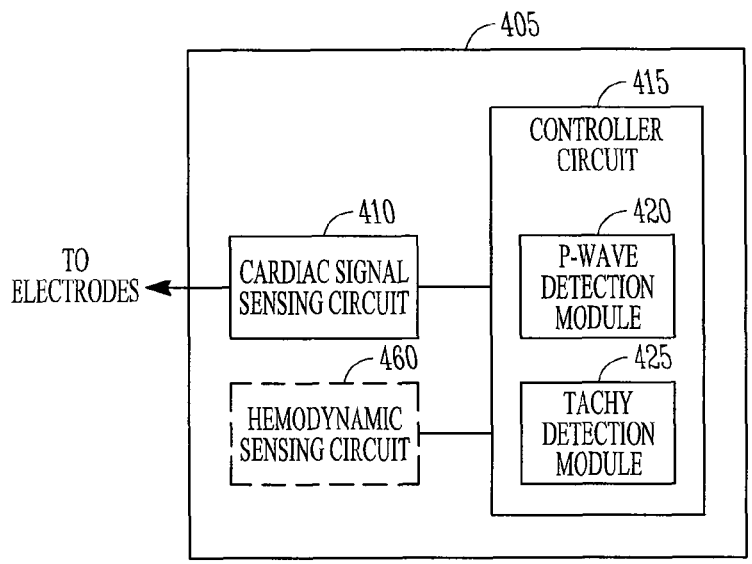
FIG. 4 is a block diagram of portions of an example of an implantable CFM device used to detect tachyarrhythmia.

FIG. 4 is a block diagram of portions of an example of an implantable cardiac function management (CFM) device 405 such as an IMD. The CFM device 405 is used to detect tachyarrhythmia. The CFM device 405 includes an implantable cardiac signal sensing circuit 410 to provide a sensed near-field depolarization signal from a ventricle and to provide a sensed a far-field intrinsic atrial signal using a far-field atrial sensing channel. The CFM device 405 also includes a controller circuit 415 communicatively coupled to the cardiac signal sensing circuit 410. The communicative coupling allows the controller circuit 415 and the cardiac signal sensing circuit 410 to communicate using electrical signals even though there can be intervening circuitry between the controller circuit 415 and the cardiac signal sensing circuit 410.

The controller circuit 415 can include a digital signal processor, application specific integrated circuit (ASIC), microprocessor, or other type of processor, interpreting or executing instructions in software or firmware. In some examples, the controller circuit 415 can include a state machine or sequencer that is implemented in hardware circuits. The controller circuit 415 can include any combination of hardware, firmware, or software, and can include one or more modules to perform the functions described herein.

To provide the functions described herein, the controller circuit 415 includes modules. A module can include software, hardware, firmware or any combination thereof. For example, the module can include instructions in software executing on or interpreted by the controller circuit 415. Multiple functions can be performed by one or more modules.

The controller circuit 415 includes a P-wave detection module 420 to detect an atrial depolarization in the sensed far-field intrinsic atrial signal, and includes a tachyarrhythmia detection module 425 to detect an episode of tachyarrhythmia using the sensed near field depolarization signal. The tachyarrhythmia detection module 425 determines whether the tachyarrhythmia episode is indicative of SVT using the detected atrial depolarization and the sensed near-field depolarization signal.

According to some examples, the cardiac signal sensing circuit 410 is communicatively coupled to a far-field atrial sensing channel that includes a unipolar sensing vector. Returning to FIG. 1, in some examples, the unipolar sensing vector includes the coil electrode 116 configured to be placed in or near an SVC and an electrode incorporated into the housing of the IMD 105. In some examples, the unipolar sensing vector includes a ring electrode 132 configured to be placed in or near the SVC and the electrode incorporated into the housing of the IMD 105. In some examples, the unipolar sensing vector includes a ring electrode 134 placed at, or proximal to, an ostium near the CS and the electrode incorporated into the housing of the IMD 105.

According to some examples, the cardiac signal sensing circuit 410 is communicatively coupled to a far-field atrial sensing channel that includes a bipolar sensing vector. In some examples, the bipolar sensing vector includes the SVC coil electrode 116 and the SVC ring electrode 132. In some examples, the bipolar sensing vector includes the SVC ring electrode 132 and the CS proximal ring electrode 134. The cardiac signal sensing circuit 410 can be coupled to a plurality of electrode combinations that provide a plurality of far-field atrial sensing channels.

Figure 5:
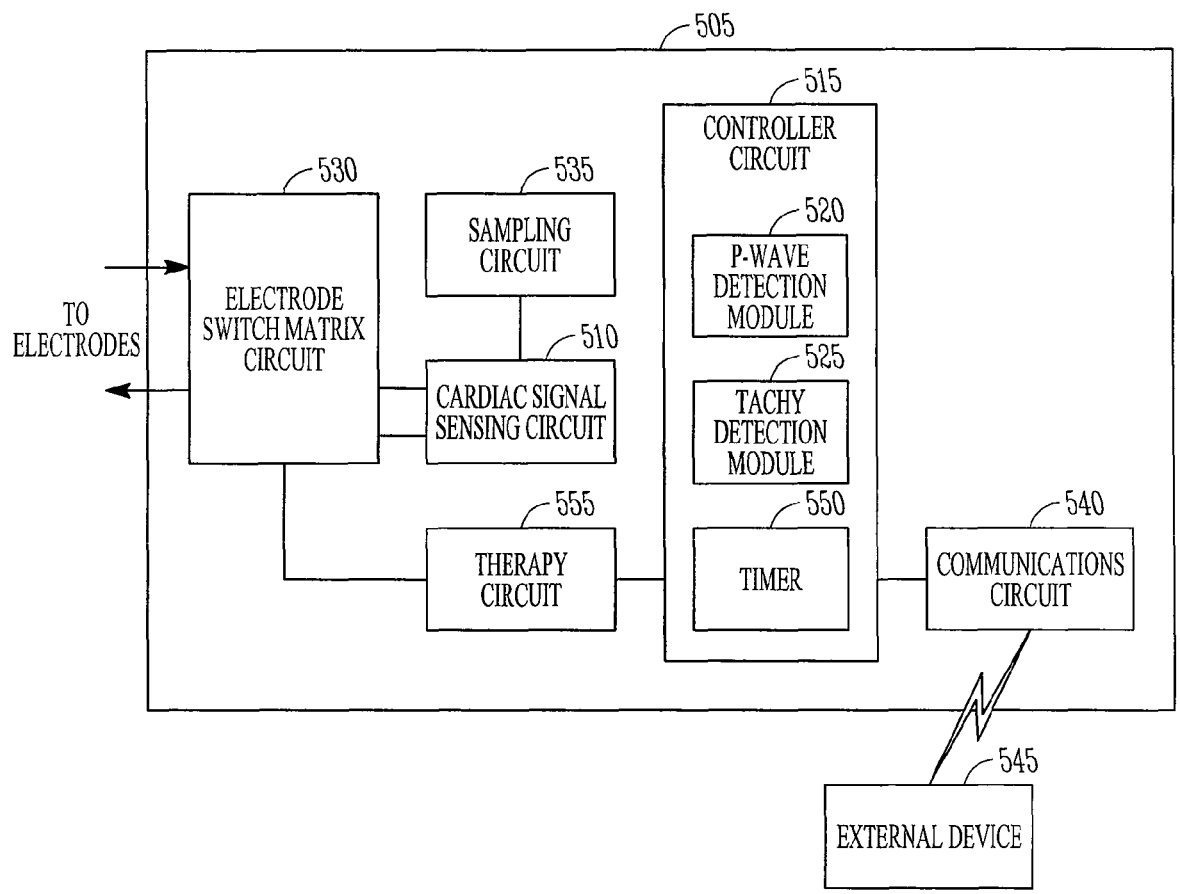
FIG. 5 is a block diagram of portions of another example of a CFM device used to detect tachyarrhythmia.

FIG. 5 is a block diagram of portions of another example of a CFM device 505 to detect tachyarrhythmia. The CFM device 505 includes a controller circuit 515 having a P-wave detection module 520 and a tachyarrhythmia detection module 525. The CFM device 505 also includes an implantable cardiac signal sensing circuit 510. The cardiac signal sensing circuit 510 is communicatively coupled to a plurality of far-field atrial sensing channels, each configured to obtain a sensed far-field intrinsic atrial signal. The far-field atrial sensing channels can include any of the electrodes combinations described herein. In certain examples, the CFM device 505 includes an electrode switch matrix circuit 530 to select a combination of electrodes to provide a far-field atrial sensing channel.

According to some examples, the CFM device 505 determines whether to switch to another configuration of sensing electrodes. The controller circuit 515 switches from a first far-field atrial sensing channel to a second far-field atrial sensing channel to improve sensing of the far-field intrinsic atrial signal. In some examples, the P-wave detection module 520 measures a feature of an atrial depolarization detected using the first far-field atrial sensing channel and to measure the feature of the atrial depolarization detected using the second far-field atrial sensing channel. The feature can be, among other things, the amplitude of the sensed far-field intrinsic atrial signal or the time duration of the sensed far-field intrinsic atrial signal.

The controller circuit 515 switches from the first far-field atrial sensing channel to the second far-field atrial sensing channel according to the measurements of the feature of the detected atrial depolarization (e.g., the controller circuit 515 switches from the first far-field atrial sensing channel to the second far-field atrial sensing channel when signals sensed using the second far-field atrial sensing channel exhibit improved signal amplitude relative to the first far-field atrial sensing channel). The reconfiguration of electrodes can be confirmed by the physician during a subsequent retrospective tachyarrhythmia episode review.

According to some examples, a second device determines whether to switch the CFM device 505 to another configuration of sensing electrodes. The far-field signal feature analysis is performed by the second device rather than the P-wave detection module 520. In some examples, the CFM device 505 includes a sampling circuit 535 communicatively coupled to the cardiac signal sensing circuit 510. The sampling circuit 535 provides a sampled far-field atrial signal from a far-field intrinsic atrial signal sensed by the cardiac signal sensing circuit 510. The CFM device 505 also includes a communication circuit 540 communicatively coupled to the controller circuit 515. The communication circuit 540 communicates information with an external device 545.

The controller circuit 515 communicates, to the external device 545, a first sampled far-field atrial signal obtained using the first far-field atrial sensing channel and a second sampled far-field atrial signal obtained using the second far-field atrial sensing channel. The controller circuit 515 switches the sensing by the cardiac signal sensing circuit 510 from the first far-field atrial sensing channel to the second far-field atrial sensing channel according to a signal communicated from the external device 545.

The far-field signals sensed from the far-field atrial sensing channels described herein can be subject to interference from cardiac signals caused by depolarization of the ventricles (e.g., a QRS complex) and repolarization of the ventricles (e.g., a T-wave) which complicates extraction of the P-wave from the far-field signal. To ensure proper sensing of the P-wave these sources of interference need to be handled appropriately.

Signal filtering of the sensing channels can be used to reduce the interference. The cardiac signal sensing circuit 510 can include a filter circuit to implement a band-pass filter. P-waves typically have lower frequencies than the QRS complex. The filter circuit should be designed such that the high-pass corner frequency is low enough to ensure minimal attenuation of the P-wave. The low-pass corner frequency needs to be set at a level where the QRS complex of the ventricular depolarization signal is maximally attenuated.

Another approach to improve sensing of the P-wave is proper setting of the noise floor of the cardiac signal sensing circuit 510. Once the noise floor is determined, a high sensitivity should be used to avoid under-sensing of the P-waves.

A further approach to improve sensing of the P-wave is to avoid far-field over-sensing of P-waves. The P-wave detection module 520 can implement one or more methods to avoid this over-sensing. In some examples, the P-wave detection module 520 implements an atrial cross-chamber hard blanking algorithm. The controller circuit 515 includes a timer circuit 550 and the P-wave detection module 520 disallows sensing of the far-field atrial signal during a time duration following a sensed near-field event. Once a near-field ventricular event is sensed, a hard blanking period timed by the timer circuit 550 begins. During the hard blanking period, far-field atrial sensing by the far-field atrial sensing channels is disabled by the P-wave detection module 520. The P-wave detection module 520 resumes the sensing when the hard-blanking period ends.

In some examples, the P-wave detection module 520 implements atrial cross-chamber soft blanking. The P-wave detection module 520 changes a sensing threshold during a time duration following a sensed near-field event. The sensed near-field event can be a ventricular event sensed using a near-field channel. For example, the near-field channel can be the bipolar electrode pair including the RV tip electrode 320A and the ring electrode 320B in FIG. 3 and the far-field sensing channel can include the SVC coil electrode 316 and the can electrode. The sensing threshold is used for sensing the far-field atrial signal. For example, if the P-wave detection module 520 uses amplitude to detect the P-wave, the threshold is an amplitude value. If the P-wave detection module 520 uses signal power to detect the P-wave, the threshold is a signal power value.

Upon detection of the near-field event by the near-field channel, the P-wave detection module 520 begins a cross chamber refractory period during which the sensing threshold is changed to a soft blanking threshold. In certain examples, the soft blanking threshold is the average amplitude of a specified number of R-waves previously detected by the far-field channel (e.g., the SVC-to-can channel). A signal would be sensed by the far-field channel during the soft blanking period if it exceeded the average R-wave amplitude. The near-field sensing channel in the RV provides reliable timing for the soft blanking period relative to the R-wave. The soft blanking ignores the QRS complex in the far-field channel while still being able to sense true P-waves.

In some examples, the P-wave detection module 520 implements rejection of the QRS signal complex. The P-wave detection module 520 allows sensing of the far-field atrial signal, but ignores far-field events sensed in the far-field atrial sensing channel during a time duration following a sensed near-field event. When a near-field event is sensed in the near-field channel, the P-wave detection module 520 begins a far-field rejection timing window. Any far-field events sensed during this timing window are ignored. For example, when a near-field ventricular event is sensed using a ventricular near-field channel, any sensed atrial event is ignored during the timing window.

In some examples, the P-wave detection module 520 performs principle component analysis (PCA) to extract the atrial depolarization from the ventricular events. If the tachyarrhythmia includes an accelerated ventricular depolarization rate, the QRS complex or the T-wave can be superimposed on the P-wave. PCA can detect the P-wave reliably, but at the expense of extra computational demand.

According to some examples, the far-field P-wave sensing by the far-field atrial sensing channel is triggered by a first event. In some examples, the controller circuit 515 is configured to initiate sensing of the far-field intrinsic atrial signal after the tachyarrhythmia detection module 525 detects the episode of tachyarrhythmia. In some examples, the tachyarrhythmia detection module 525 detects the episode of tachyarrhythmia when detecting a rate of sensed ventricular depolarizations that exceeds a lowest tachyarrhythmia rate threshold. In some examples, the tachyarrhythmia detection module 525 detects the episode of tachyarrhythmia when detecting a rate of sensed ventricular depolarizations that is within a threshold rate below a lowest tachyarrhythmia rate threshold (e.g., a sub-tachyarrhythmia rate zone).

In some examples, the tachyarrhythmia detection module 525 detects the episode of tachyarrhythmia without comparison to a lowest tachyarrhythmia rate threshold. The tachyarrhythmia detection module 525 can detect the episode of tachyarrhythmia when detecting a sudden change in a rate of sensed ventricular depolarizations. The sudden change includes a detected change in rate of sensed ventricular depolarization that exceeds a threshold change in rate within a specified time duration. Descriptions of systems, devices, and methods to detect tachyarrhythmia without a comparison to a specified lowest tachyarrhythmia rate are found in Kim et al., U.S. Patent Publication No. 20070135848, "Zoneless Tachyarrhythmia Detection with Real Time Rhythm Monitoring, filed Dec. 13, 2005, which is incorporated herein in its entirety.

Once the far-field atrial signal is sensed, dual-chamber arrhythmia detection features are available for a single chamber device. The tachyarrhythmia detection module 525 determines whether the tachyarrhythmia episode is indicative of SVT using the detected atrial depolarization.

According to some examples, the tachyarrhythmia detection module 525 determines whether the tachyarrhythmia episode is indicative of SVT by comparing a ventricular depolarization rate determined from the depolarization signal to an atrial depolarization rate determined from the far-field intrinsic atrial signal. If the ventricular depolarization rate tracks, or nearly tracks, the atrial depolarization rate, the episode is deemed to be SVT. If the ventricular depolarization rate exceeds the atrial depolarization rate by a threshold rate value, the episode is deemed to be VT.

In some examples, the tachyarrhythmia detection module 525 determines whether the tachyarrhythmia episode is indicative of VT by measuring a timing interval from the detected atrial depolarization to a corresponding detected ventricular depolarization. Stability of the measured interval can indicate that the episode is SVT.

According to some examples, the tachyarrhythmia detection module 525 determines whether the tachyarrhythmia episode is indicative of VT using a measure of at least one of ventricular rate or ventricular morphology together with a measure of at least one of atrial rate, atrial interval stability, or P-wave morphology regularity.

In an illustrative example, VT can be detected by comparing sensed P-waves and sensed R-waves. A sudden high ventricular rate with dissociation between P-waves and R-waves can indicate tachycardia. A description of systems and methods that detect tachycardia using rate channels is found in Gilkerson, et al., U.S. Pat. No. 6,522,925, "System and Method for Detection Enhancement Programming," filed May 13, 2000, which is incorporated herein by reference.

In another example, a sudden high heart rate together with atrial interval instability can indicate VT. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

In still another example, the tachyarrhythmia detection module 525 determines whether the tachyarrhythmia episode is indicative of atrial fibrillation. Atrial fibrillation can be detected using a measure of atrial and ventricular rate, a measure of ventricular rate stability, or using morphology information. For example, the tachyarrhythmia detection module 525 can determine atrial fibrillation when an atrial rate exceeds an atrial fibrillation rate threshold and the ventricular rate is unstable. Descriptions of methods to discriminate atrial fibrillation (AF) from atrial flutter (AFL), or from SVT, using a measure of complexity are found in Li et al., "Method and Apparatus for Cardiac Arrhythmia Classification Using Sample Entropy," U.S. Patent Pub. No. 20060281999, filed Jun. 13, 2005, which is incorporated herein by reference in its entirety.

The far-field atrial signal can be used to for atrial morphology analysis to better recognize and classify atrial tachyarrhythmia. This is especially true of the far-field sensing channel includes a unipolar configuration. Such far-field signal sensing can be more reliable than near-field sensing. In some examples, the atrial far-field morphology can be stored and analyzed in the CFM device 505.

According to some examples, the CFM device 505 includes a therapy circuit 555 communicatively coupled to the controller circuit 515 to provide anti-tachyarrhythmia therapy. The tachyarrhythmia detection module 525 is configured to provide a determination whether the episode of tachyarrhythmia is indicative of VT or SVT. According to the determination by the tachyarrhythmia detection module 525, the controller circuit 515 initiates an anti-tachyarrhythmia therapy according to the determination.

In some examples, if the tachyarrhythmia detection module 525 determines that the tachyarrhythmia is VT, the controller circuit 515 initiates delivery of therapy to the subject. In certain examples the therapy circuit 555 provides a high energy electrical shock to the heart (e.g., defibrillation). In certain examples the therapy circuit 555 provides anti-tachycardia pacing (ATP). ATP uses lower energy pacing energy to establish a regular rhythm in a heart. This allows the tachycardia to be converted to a normal heart rhythm without exposing the patient to high energy defibrillation therapy that can be painful to the patient. In certain examples, the therapy circuit 555 is able to provide both ATP and defibrillation. When VT is detected, the device can try to convert the arrhythmia with ATP before resorting to high energy defibrillation.

In certain examples, the tachyarrhythmia detection module 525 is configured to provide a determination whether the episode of tachyarrhythmia is indicative of atrial fibrillation, atrial flutter, or atrial tachycardia. Based on the determination, the controller circuit 515 initiates an anti-tachyarrhythmia therapy using the therapy circuit 555, such as ATP.

The sensed P-waves can also be reviewed retrospectively by a physician. Sampled far-field P-waves can be transmitted to the external device 545. The external device 545 can include an IMD programmer or a remote patient management system. Additional information such as, among other things, atrial rate, atrial interval instability measurements, and P-wave morphology regularity analysis can also be transmitted to the external device 545. Far-filed or near-field signals transmitted to the external device 545 can be annotated to indicate any episodes of VT and SVT.

In certain examples, the CFM device 505 includes a memory and the information is stored in log form in the CFM device. One or more log entries can be sent to the external device. The log entries can be used by the physician to determine a morphology template of an episode such as an SVT episode. The log entries can also be used by the physician to assess how the detection algorithm performs and whether a change needs to made to the detection algorithm implemented in the CFM device 505.

Returning to FIG. 4, in some examples the CFM device 405 includes an implantable hemodynamic sensor circuit 460 communicatively coupled to the controller circuit 405. The hemodynamic sensor circuit 460 provides a hemodynamic signal other than an intrinsic electrical cardiac signal.

The hemodynamic signal is obtained from a sensor or sensors that monitor mechanical function of the heart. Examples include, among other things, sensors to monitor pressure, cardiac temperature, intracadiac impedance, heart sounds, heart valve motion, ventricular wall motion, and cardiac strain. The sensors provide hemodynamic signals that represent the mechanical functionality of the cardiovascular system. It should be noted this is different from sensing electrical intrinsic cardiac signals which are the action potentials that propagate through the heart's electrical conduction system. The tachyarrhythmia detection module 425 determines whether the tachyarrhythmia episode is indicative of SVT using the atrial depolarization detected in the far-field signal, the sensed near-field signal from the ventricle, and the sensed hemodynamic signal.

For example, a pressure sensor can be implanted in a coronary vessel to determine LV pressure by direct measurement of coronary vessel pressure. Because the pressure sensor varies its output with changes in pressure as occur during heart chamber expansions and contractions, the pressure can provide a signal indicative of activity of the heart. A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference. The tachyarrhythmia detection module 425 uses the additional information provided by a hemodynamic sensor, such as a pressure sensor, to determine if the tachyarrhythmia is VT.

The devices, systems, and methods described allow a single chamber ICD such as shown in FIG. 3 to provide virtual dual chamber tachyarrhythmia detection. This provides improved tachyarrhythmia detection for patients who may not need atrial pacing support, and allows dual chamber signal history and annotation for review by a physician. The far-field sensing of atrial signals also allows far-field electrograms that can provide useful morphological information for use by tachyarrhythmia detection algorithms to recognize different types of atrial arrhythmias.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
an implantable cardiac signal sensing circuit, configured to provide a sensed near-field depolarization signal from a ventricle and to provide a sensed far-field intrinsic atrial signal using at least one of a first far-field atrial sensing channel and a second far-field sensing channel, wherein a far-field atrial sensing channel is configured to receive the far-field intrinsic atrial signal from an electrode location that is outside of an atrium; and
a controller circuit communicatively coupled to the cardiac signal sensing circuit, wherein the controller circuit includes:
a P-wave detection module configured to detect an atrial depolarization in the sensed far-field intrinsic atrial signal;
switch from the first far-field atrial sensing channel to a second far-field atrial sensing channel according to a measurement of the detected atrial depolarization; and
a tachyarrhythmia detection module configured to detect an episode of tachyarrhythmia using the sensed near-field ventricular depolarization signal and to determine whether the tachyarrhythmia episode is indicative of supraventricular tachycardia (SVT) using at least one of atrial rate or atrial interval determined using the far-field detected atrial depolarization and using the sensed near-field ventricular depolarization signal.

2. The apparatus of claim 1,
wherein the P-wave detection module is configured to measure a feature of a atrial depolarization detected using the first far-field atrial sensing channel and to measure the feature of the atrial depolarization detected using the second far-field atrial sensing channel, and
wherein the controller circuit is configured to switch from the first far-field atrial sensing channel to the second far-field atrial sensing channel according to the measurements of the feature of the detected atrial depolarization.

3. The apparatus of claim 1, including:
a sampling circuit, communicatively coupled to the cardiac signal sensing circuit, configured to provide a sampled far-field atrial signal from a sensed far-field intrinsic atrial signal; and
a communication circuit, communicatively coupled to the controller circuit, configured to communicate information with an external device, and
wherein the controller circuit is configured to:
communicate, to the external device, a first sampled far-field atrial signal obtained using the first far-field atrial sensing channel and a second sampled far-field atrial signal obtained using the second far-field atrial sensing channel; and
switch from the first far-field atrial sensing channel to the second far-field atrial sensing channel according to a signal communicated from the external device.

4. The apparatus of claim 1, wherein the cardiac signal sensing circuit and the controller circuit are included in an implantable cardiac function management (CFM) device, and wherein the far-field atrial sensing channel includes at least one of:
a unipolar sensing vector electrode configuration including a coil electrode configured to be placed in or near a superior vena cava (SVC) and an electrode incorporated into a housing of the CFM device;
a unipolar sensing vector electrode configuration including a ring electrode configured to be placed in or near the SVC and the electrode incorporated into the housing of the CFM device;
a unipolar sensing vector electrode configuration including a ring electrode configured to be placed at, or proximal, to an ostium near a coronary sinus (CS), and the electrode incorporated into the housing of the CFM device;
a bipolar sensing vector electrode configuration including the SVC coil electrode and the SVC ring electrode; and
a bipolar sensing vector electrode configuration including the SVC ring electrode and the CS proximal ring electrode.

5. The apparatus of claim 1, wherein the controller circuit includes a timer circuit, and
wherein the P-wave detection module is configured to help reduce or avoid over-sensing of the far-field intrinsic atrial signal by at least one of:
disallowing sensing of the far-field atrial signal during a time duration following a sensed near-field event,
changing a sensing threshold during a time duration following the sensed near-field event, wherein the sensing threshold is used for sensing the far-field atrial signal, or
allowing sensing of the far-field atrial signal, but ignoring events sensed in the far-field atrial sensing channel during a time duration following the sensed near-field event.

6. The apparatus of claim 1, wherein the P-wave detection module is configured to perform principle component analysis (PCA) to extract the atrial depolarization from the ventricular events.

7. The apparatus of claim 1, wherein the controller circuit is configured to initiate sensing of the far-field intrinsic atrial signal after the tachyarrhythmia detection module detects the episode of tachyarrhythmia.

8. The apparatus of claim 1, wherein the controller circuit is configured to initiate sensing of the far-field intrinsic atrial signal when the tachyarrhythmia detection module detects a rate of sensed ventricular depolarization that exceeds a lowest tachyarrhythmia rate threshold value.

9. The apparatus of claim 1, wherein the controller circuit is configured to initiate sensing of the far-field intrinsic atrial signal when the tachyarrhythmia detection module detects a sudden change in a rate of sensed ventricular depolarizations, wherein detecting the sudden change includes detecting a change in rate of sensed ventricular depolarizations that exceeds a threshold change in rate within a specified time duration.

10. The apparatus of claim 1, wherein the tachyarrhythmia detection module is configured to determine whether the tachyarrhythmia episode is indicative of SVT using:
a measure of at least one of ventricular rate or ventricular morphology; and
a measure of at least one of atrial rate, atrial interval stability, or P-wave morphology regularity.

11. The apparatus of claim 1, wherein the tachyarrhythmia detection module is configured to determine whether the tachyarrhythmia episode is indicative of SVT by at least one of:
comparing a ventricular depolarization rate determined from the depolarization signal to an atrial depolarization rate determined from the far-field intrinsic atrial signal, or measuring a timing interval from the detected atrial depolarization to a corresponding detected ventricular depolarization.

12. The apparatus of claim 1, wherein the tachyarrhythmia detection module is configured to determine whether the tachyarrhythmia episode is indicative of atrial fibrillation using the detected atrial depolarization and the sensed near-field depolarization signal.

13. The apparatus of claim 1, including:
an implantable hemodynamic sensor circuit communicatively coupled to the controller circuit, wherein the hemodynamic sensor circuit provides a hemodynamic signal, other than an intrinsic electrical cardiac signal, and wherein the hemodynamic signal is representative of mechanical function of a cardiovascular system of a subject; and
wherein the tachyarrhythmia detection module is configured to determine whether the tachyarrhythmia episode is indicative of SVT using the hemodynamic signal.

14. The apparatus of claim 1, including a therapy circuit, communicatively coupled to the controller circuit, configured to provide anti-tachyarrhythmia therapy,
wherein the tachyarrhythmia detection module is configured to provide a determination whether the episode of tachyarrhythmia is indicative of VT or SVT, and
wherein the controller circuit is configured to initiate an anti-tachyarrhythmia therapy according to the determination.

15. The apparatus of claim 1, including a therapy circuit, communicatively coupled to the controller circuit, configured to provide anti-tachyarrhythmia therapy,
wherein the tachyarrhythmia detection module is configured to provide a determination whether the episode of tachyarrhythmia is indicative of one of atrial fibrillation, atrial flutter, or atrial tachycardia, and
wherein the controller circuit is configured to initiate an anti-tachyarrhythmia therapy according to the determination.

16. A method comprising:
sensing a far-field intrinsic atrial signal with an implantable cardiac function management (CFM) device, wherein the far-field intrinsic atrial signal is sensed using a first far-field atrial sensing channel configured to receive the far-field intrinsic atrial signal from an electrode located outside of an atrium;
detecting an atrial depolarization in the sensed far-field intrinsic atrial signal;
switching from the first far-field atrial sensing channel to a second far-field atrial sensing channel according to a measurement of the detected atrial depolarization;
detecting an episode of tachyarrhythmia using a near-field depolarization signal sensed from a ventricle; and
determining whether the tachyarrhythmia episode is indicative of supraventricular tachycardia (SVT) using at least one of atrial rate or atrial interval determined using the far-field detected atrial depolarization and the sensed near-field depolarization signal from the ventricle.

17. The method of claim 16, including:
sampling the far-field intrinsic atrial signal sensed with the first far-field atrial sensing channel to obtain a first sampled far-field atrial signal;
sampling a far-field intrinsic atrial signal sensed with the second far-field atrial sensing channel to obtain a second sampled far-field atrial signal;
communicating the first and second sampled far-field atrial signals to an external device; and wherein switching from the first far-field atrial sensing channel to a second far-field atrial sensing channel includes switching from the first far-field atrial sensing channel to a second far-field atrial sensing channel according to a signal communicated from the external device.

18. The method of claim 16, wherein the first far-field atrial sensing channel and the second far-field atrial sensing channel are selected from the group consisting essentially of:
a unipolar sensing vector electrode configuration including a coil electrode configured to be placed in or near a superior vena cava (SVC) and an electrode incorporated into a housing of the ICD;
a unipolar sensing vector electrode configuration including a ring electrode configured to be placed in or near the SVC and the electrode incorporated into a housing of the ICD;
a unipolar sensing vector electrode configuration including a ring electrode configured to be placed at, or proximal, to an ostium near a coronary sinus (CS), and the electrode incorporated into a housing of the ICD;
a bipolar sensing vector electrode configuration including the SVC coil electrode and the SVC ring electrode; and
a bipolar sensing vector electrode configuration including the SVC ring electrode and the CS proximal ring electrode.

19. The method of claim 16, wherein detecting an atrial depolarization includes rejecting ventricular events sensed by the first far-field atrial sensing channel.

20. The method of claim 19, wherein rejecting ventricular events includes at least one of:
disallowing sensing during a time duration following sensing of a near-field event in a ventricle,
changing a sensing threshold during a time duration following sensing of a near-field event in a ventricle,
allowing sensing but ignoring events sensed during a time duration following sensing of a near-field event in a ventricle, or
performing principle component analysis (PCA) to extract the atrial depolarization from the ventricular events.

21. The method of claim 16, wherein sensing a far-field intrinsic atrial signal includes sensing the far-field intrinsic atrial signal when the episode of tachyarrhythmia is detected.

22. The method of claim 16, wherein sensing a far-field intrinsic atrial signal includes sensing the far-field intrinsic atrial signal when a rate of sensed ventricular depolarization exceeds a threshold rate.

23. The method of claim 16, wherein sensing a far-field intrinsic atrial signal includes sensing the far-field intrinsic atrial signal when detecting a sudden change in rate of sensed ventricular depolarizations, wherein detecting the sudden change includes detecting a change in rate of sensed ventricular depolarizations that exceeds a threshold change in rate within a specified time duration.

24. The method of claim 16, wherein determining whether the tachyarrhythmia episode is indicative of SVT includes using:
a measure of at least one of ventricular rate or a measure of ventricular morphology; and
a measure of at least one of atrial rate, atrial interval stability, or P-wave morphology regularity.

25. The method of claim 16, wherein determining whether the tachyarrhythmia episode is indicative of SVT includes at least one of:

comparing a ventricular depolarization rate determined from the depolarization signal to an atrial depolarization rate determined from the far-field intrinsic atrial signal, or measuring a timing interval from the detected atrial depolarization to a corresponding ventricular depolarization.

26. The method of claim 16, including determining whether the tachyarrhythmia episode is indicative of atrial fibrillation using the detected atrial depolarization and the sensed near-field depolarization signal.

27. The method of claim 16, wherein determining whether the tachyarrhythmia episode is indicative of SVT includes determining using the detected atrial depolarization, the sensed near-field depolarization signal from the ventricle, and a hemodynamic signal representative of mechanical function of a cardiovascular system of a subject.

* * * * *